(12) United States Patent
Avouris et al.

(10) Patent No.: US 9,759,643 B2
(45) Date of Patent: *Sep. 12, 2017

(54) METHOD AND INTEGRATED DEVICE FOR ANALYZING LIQUID FLOW AND LIQUID-SOLID INTERFACE INTERACTION

(71) Applicant: International Business Machines Corporation, Armonk, NY (US)

(72) Inventors: Phaedon Avouris, Yorktown Heights, NY (US); Michael Engel, Ossining, NY (US); Claudius Feger, Poughkeepsie, NY (US); Ronaldo Giro, Rio de Janeiro (BR); Rodrigo Ferreira, Rio de Janeiro (BR); Mathias Steiner, Rio de Janeiro (BR)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/001,321

(22) Filed: Jan. 20, 2016

(65) Prior Publication Data

US 2016/0139019 A1  May 19, 2016

Related U.S. Application Data

(62) Division of application No. 14/502,897, filed on Sep. 30, 2014, now Pat. No. 9,310,285.

(51) Int. Cl.
*G01N 11/04* (2006.01)
*G01N 21/71* (2006.01)
(Continued)

(52) U.S. Cl.
CPC ............. *G01N 11/04* (2013.01); *G01N 21/71* (2013.01); *G01N 33/24* (2013.01);
(Continued)

(58) Field of Classification Search
CPC ............. G06F 2217/16; G06F 17/5072; G06F 17/5009; G01N 33/24; G01N 2201/08;
(Continued)

(56) References Cited

U.S. PATENT DOCUMENTS 8,395,774 B2  3/2013  Afzali
2011/0247934 A1*  10/2011  Wang ................ B01L 3/502792
204/450

(Continued)

FOREIGN PATENT DOCUMENTS

WO  WO2013116675  8/2013

OTHER PUBLICATIONS

N. S. K. Gunda, B. Bera, N. K. Karadimitriou, S. K. Mitra, S. M. Hassanizadeh, "Reservoir-on-a-Chip (ROC): A new paradigm in reservoir engineering", Lab Chip 11, 3785 (2011).

(Continued)

*Primary Examiner* — Evan Pert
*Assistant Examiner* — Changhyun Yi
(74) *Attorney, Agent, or Firm* — Law Office of Charles W. Peterson, Jr.; Louis J. Percello, Esq.

(57) ABSTRACT

An Integrated Circuit (IC) chip with a lab-on-a-chip, a method of manufacturing the lab-on-a-chip and a method of using the lab-on-a-chip for fluid flow analysis in physical systems through combination with computer modeling. The lab-on-a-chip includes cavities in a channel layer and a capping layer, preferably transparent, covering the cavities. Gates control two dimensional (2D) lattice structures acting as heaters, light sources and/or sensors in the cavities, or fluid channels. The gates and two dimensional (2D) lattice structures may be at the cavity bottoms or on the capping layer. Wiring connects the gates and the 2D lattice structures externally.

7 Claims, 6 Drawing Sheets

(51) Int. Cl.
| | |
|---|---|
| G06F 17/50 | (2006.01) |
| G01N 33/24 | (2006.01) |
| H01L 29/16 | (2006.01) |
| H01L 29/49 | (2006.01) |
| G01N 11/00 | (2006.01) |

(52) U.S. Cl.
CPC ...... *G06F 17/5009* (2013.01); *G06F 17/5072* (2013.01); *H01L 29/1606* (2013.01); *H01L 29/4966* (2013.01); *G01N 2011/008* (2013.01); *G01N 2201/08* (2013.01); *G06F 2217/16* (2013.01)

(58) Field of Classification Search
CPC .. G01N 21/71; G01N 11/04; G01N 2011/008; H01L 29/1606; H01L 29/4966
USPC .......................... 345/633; 435/6.12; 438/478
See application file for complete search history.

(56) References Cited

U.S. PATENT DOCUMENTS

| | | |
|---|---|---|
| 2011/0272671 A1 | 11/2011 | Skiba-Szymanska et al. |
| 2012/0149021 A1* | 6/2012 | Yung ........................ B03C 1/01 435/6.12 |
| 2012/0212242 A1 | 8/2012 | Masel |
| 2013/0018599 A1 | 1/2013 | Peng |
| 2013/0256683 A1 | 10/2013 | Imanishi |
| 2013/0328016 A1 | 12/2013 | Guo |
| 2013/0334579 A1 | 12/2013 | Accardi |
| 2015/0206796 A1 | 7/2015 | Dasgupta et al. |
| 2016/0004298 A1* | 1/2016 | Mazed ..................... G06F 3/013 345/633 |

OTHER PUBLICATIONS

K. Choi, A. H.C. Ng, R. Fobel, A. R. Wheeler "Digital Microfluidics", Annu. Rev. Anal. Chem. 5, 413 (2012).
T. Cubaud, U. Ulmanella, C.-M. Ho, "Two-phase flow in microchannels with surface modifications", Fluid Dynamics Research 38, 772 (2006).
J. Sun, Y. L. He, W. Q. Tao, J. W. Rose, H. S. Wang, "Multi-scale study of liquid flow in micro/nanochannels: effects of surface wettability and topology", Microfluid Nanofluid 12, 991 (2012).
J. S. Suh, R. Greif, C. P. Grigoropoulos "Friction in microchannel flows of a liquid and vapor in trapezoidal and sinusoidal grooves" International Journal of Heat and Mass Transfer 44, 3103 (2001).
F. Sofos, T. E Karakasidis, A. Liakopoulos, "Surface wettability effects on flow in rough wall nanochannels", Microfluid Nanofluid 12, 25 (2012).
N. S. K. Gunda, J. Joseph, A. Tamayol, M. Akbar, S. K. Mitra, "Measurement of pressure drop and flow resistance in microchannels with integrated micropillars", Microfluid Nanofluid 14, 711 (2013).
N. V. Priezjev, S. M. Troian, "Influence of periodic wall roughness on the slip behaviour at liquid/solid interfaces: molecular-scale simulations versus continuum predictions", J. Fluid Mech. 554, 25 (2006).
X. Tan, Z. Zhou, M. M. C. Cheng, "Electrowetting on dielectric experiments using graphene", Nanotechnology 23, 375501 (2012).
X. B. Tan, P. Zeng, W. W. Yi, M. M. C. Cheng "Graphene based digital microelectronics", MEMS 2013, Taipei, Taiwan, Jan. 20-24, 2013.
P. K. Ang,.A. Li, M. Jaiswal, Y. Wang, H. W. Hou,J. T. L. Thong, C. T. Lim, K. P. Loh "Flow Sensing of Single Cell by Graphene Transistor in a Microfluidic Channel" Nano Lett. 11, 5240 (2011).
R. X. He, P. Lin, Z. K. Liu, H. W. Zhu, X. Z. Zhao, H. L. W. Chan, F. Yan, "Solution-Gated Graphene Field Effect Transistors Integrated in Microfluidic Systems and Used for Flow Velocity Detection" Nano Letters 12, 1404 (2012).
A. K. M. Newaz, D. A. Markov, D. Prasai, K. I. Bolotin, "Graphene Transistor as a Probe for Streaming Potential", Nano Lett. 12, 2931 (2012).
P. K. Ang, W. Chen, A. T. S. Wee, K. P. Loh, "Solution-Gated Epitaxial Graphene as pH Sensor" J. Am. Chem. Soc. 130, 14392 (2008).
F. Xing, Z.-B. Liu, Z.-C. Deng, X.-T. Kong, X.-Q. Yan, X.-D. Chen, Q. Ye, C.-P. Zhang, Y.-S. Chen, J.-Guo Tian "Sensitive Real-Time Monitoring of Refractive Indexes Using a Novel Graphene-Based Optical Sensor" Scientific Reports 2, 908 (2013).
S. K. Min, W. Y. Kim, Y. C. and K. S. Kim "Fast DNA sequencing with a graphene-based nanochannel device" Nature Nanotechnology 6, 162 (2011).
M. Freitag, M. Steiner, Y. Martin, V. Perebeinos, Z. Chen, J. C. Tsang, P. Avouris "Energy Dissipation in Graphene Field-Effect Transistors" Nano Lett. 9, 1883 (2009).
J. Kang, H. Kim, K. S. Kim, S.-K. Lee, S. Bae, J-H. Ahn, Y.-J. Kim, J.-B. Choi, B. H. Hong, "High-Performance Graphene-Based Transparent Flexible Heaters" Nano Lett. 11, 5154 (2011).
D. Sui, Y. Huang, L. Huang, J. Liang, Y. Ma, Y. Chen, "Flexible and Transparent Electrothermal Film Heaters Based on Graphene Materials" Small 7, 3186 (2011).
M. Freitag, H.-Y. Chiu, M. Steiner, V. Perebeinos, P. Avouris, "Thermal infrared emission from biased graphene" Nature Nanotechnology 5, 497 (2010).
M. Engel, M. Steiner, A. Lombardo, A. C. Ferrari, H. v. Löhneysen, Ph. Avouris, R. Krupke "Light—matter interaction in a microcavity-controlled graphene transistor" Nature Communications 3, 906 (2012).
R. S. Sundaram, M. Engel, A. Lombardo, R. Krupke, A. C. Ferrari, Ph. Avouris, M. Steiner, "Electroluminescence in Single Layer MoS2". Nano Lett. 13, 1416 (2013).
F. Xia, T. Mueller, R. Golizadeh-Mojarad, M. Freitag, Y.-M. Lin, J. Tsang, V. Perebeinos, P. Avouris "Photocurrent Imaging and Efficient Photon Detection in a Graphene Transistor", Nano Letters 9, 1039 (2009).
R. A. Hayes, B. J. Feenstra "Video-speed electronic paper based on electrowetting", Nature 425, 383 (2003).
R. S. Sundaram, M. Steiner, H.-Y. Chiu, M. Engel, A. A. Bol, R. Krupke, M. Burghard, K. Kern, Ph. Avouris, "The Graphene-Gold Interface and Its Implications for Nanoelectronics" Nano Letters 11, 3833 (2011).
M. Engel, M. Steiner, R. S. Sundaram, R. Krupke, A. A. Green, M. C. Hersam, Ph. Avouris, "Spatially Resolved Electrostatic Potential and Photocurrent Generation in Carbon Nanotube Array Devices", ACS Nano 6, 7303 (2012).

* cited by examiner

METHOD AND INTEGRATED DEVICE FOR ANALYZING LIQUID FLOW AND LIQUID-SOLID INTERFACE INTERACTION

CROSS REFERENCE TO RELATED APPLICATION

The present invention is a division of U.S. patent application Ser. No. 14/502,897, "METHOD AND INTEGRATED DEVICE FOR ANALYZING LIQUID FLOW AND LIQUID-SOLID INTERFACE INTERACTION" filed Sep. 30, 2014, to Phaedon Avouris et al., assigned to the assignee of the present invention and incorporated herein by reference.

BACKGROUND OF THE INVENTION

Field of the Invention

The present invention generally relates to analyzing liquid flow and liquid-solid interface interaction and more particularly to an integrated device for self-contained liquid flow and liquid-solid interface interaction analysis that enables the comparison with and the validation of computational models of such liquid solid interactions.

Background Description

Hydrocarbon fuels, e.g., oil and natural gas, are valuable commodities. It is important to understand how oil is situated and flowing in an oil field in order to make decisions about, for example, where to drill, how deep to drill, how many wells to drill, as well as how to chemically enhance hydrocarbon recovery in such fields. Thus, major resources may be expended in modeling a field to facilitate making these dimensions. While a typical computer model may be used to simulate the field, the simulations may not allow engineers to sufficiently visualize and study the relevant field properties, in particular on smaller length scales, e.g., one centimeter (1 cm) and below. Instead a model that accounts for the physical/chemical properties on much smaller length scales may be necessary. While a typical hydrocarbon reservoir model may mimic some of the typical field properties at ambient conditions on large lengths scales, e.g. meters to kilometers, to facilitate visualizing such reservoir properties to some extent, the model may not account for realistic reservoir conditions on the length scale of nanometer to millimeters, including local surface properties of solids, heat, and chemical conditions. The lack of inclusion of such conditions limits the validity and precision of state-of-the-art reservoir models. Importantly, a method enabling experimental validation is needed for the verification of such modeling conditions on nanometer to millimeter scales. Moreover, the method for modeling liquid solid interactions and the design of devices for experimentally validating such liquid solid interactions should be interconnected. Bio-engineering for healthcare applications may have many of the same requirements and needs.

While state-of-the-art modeling approaches provide for application-specific channel designs, micro-fluidic designs are not specifically geared towards exploiting structured or functionalized channel surfaces or intra-channel features. Further, while the impact of surface functionalization and patterning on liquid flow has been studied to some extent, previously intra-channel feature or surface pattern engineering for liquid flow has been done at a relatively large, metric scale, well above the micron and sub-micron scale. Thus, microscopic effects that dominate flow through porous materials such as shale or sandstone, are seldom considered.

Thus, there exists a need for devices for studying fluid flow and liquid-solid interactions, especially at the micron and sub-micron level; and more particularly, for transferring a rock pattern onto a device with integrated device functionality, such as local heaters, emitters, detectors and sensors, for quantitative, multi-scale analysis of liquid flow in porous media using a combination of simulation and experimental validation for enhanced oil recovery or for enhanced bio-engineering capabilities.

SUMMARY OF THE INVENTION

It is an aspect of the invention to facilitate studying fluid flow and liquid-solid interactions at the micron and sub-micron range;

It is another aspect of the invention to facilitate studying micron and sub-micron fluid flow and liquid-solid interactions with representative rock patterns that resemble the physical and chemical environment of the study, for example, through transfer of geometrical patterns (such as rock patterns) or suitable surface structures realized through advanced surface patterning and functionalization techniques;

It is yet another aspect of the invention to provide an integrated, self-contained device for studying micron and sub-micron fluid flow and liquid-solid interactions with representative (rock) patterns or suitable surface structures in the device that integrates on-chip functionalities such as local heaters, emitters, detectors and sensors;

The present invention relates to an Integrated Circuit (IC) chip with a lab-on-a-chip, a method of manufacturing the lab-on-a-chip and a method of using the lab-on-a-chip for fluid flow analysis in combination with computer simulations through an iterative process. The lab-on-a-chip includes cavities in a channel layer and a capping layer, preferably transparent, covering the cavities. Gates control two dimensional (2D) lattice structures acting as heaters, light sources and/or sensors in the cavities (channels), or fluid channels. The gates and two dimensional (2D) lattice structures may be at the cavity (channel) bottoms or on the capping layer. Wiring connects the gates and the 2D lattice structures externally.

BRIEF DESCRIPTION OF THE DRAWINGS

The foregoing and other objects, aspects and advantages will be better understood from the following detailed description of a preferred embodiment of the invention with reference to the drawings, in which.

DESCRIPTION OF PREFERRED EMBODIMENTS

Figure 1:
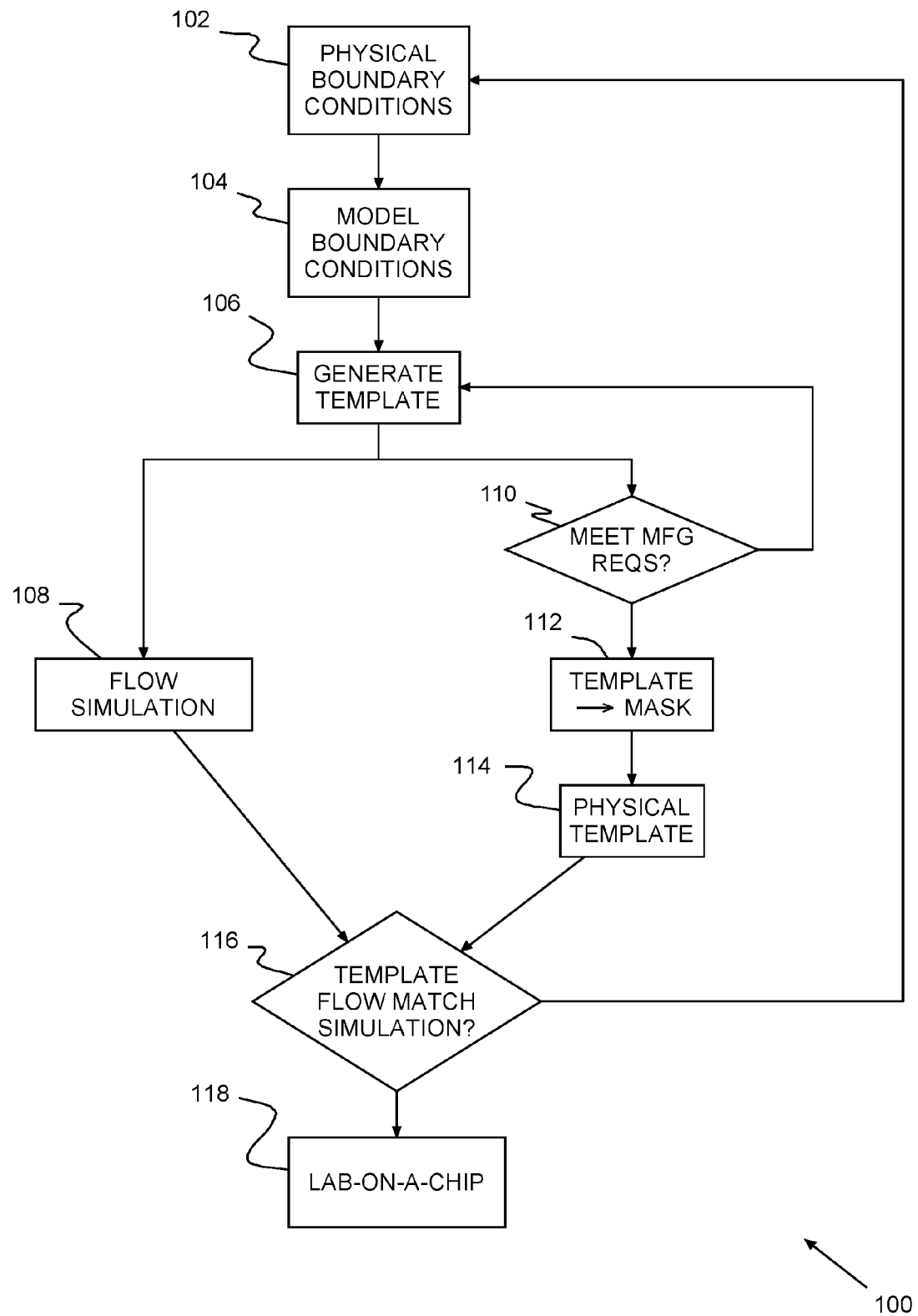
FIG. 1 shows an example of fabricating a lab-on-a-chip for simulating fluid flow according to a preferred embodiment of the present invention.

Turning now to the drawings and, more particularly, FIG. 1 shows an example 100 of fabricating a lab-on-a-chip for simulating fluid flow according to a preferred embodiment of the present invention. Essentially, the lab-on-a-chip fabrication 100 uses typical state of the art semiconductor integrated circuit fabrication techniques (e.g., CMOS chip fabrication) to form a template or templates and sufficient wiring and analysis support circuitry. The template has physical patterns that represent fluid flow in a geological space. Once formed and verified/validated, the template simulates fluid flow through fluid channels representative of the geological space. Typically the fully formed template structure is capped with a capping layer. The capping layer may include the simulation support circuitry, or the simulation support circuitry may be opposite the cap, on or in, the same semiconductor wafer supporting the template(s). Thus, the lab-on-a-chip enables liquid flow analysis through a defined space with defined properties, and experimental validation of the results on a wide range (orders of magnitude) of scale lengths under well-defined laboratory conditions, ranging from nanometers (nm) to millimeters (mm).

Fabrication begins 102 with physical information that determines the boundary system conditions. Next, transforming 104 the physical information algorithmically, equations mathematically describe the physical structures. A template file 106, created from the equations, is input to both flow simulation 108 and template manufacturing 110. Flow simulation 108 predicts the flow behavior in the geometric structure defined by the template file 106. Simultaneously, template preprocessing determines 110 specific manufacturing requirements, and provided manufacturing is feasible within manufacturing process, the template file 106 is converted 112 into a suitable format for manufacturing a physical template 114. If the template file 106 is unmanufacturable, the template file 106 may be adjusted or recreated. Comparing 116 flow simulation 108 results against the physical template 114, either the comparison results do not match and the template file 106 requires additional tweaking; or the physical template 114 is complete. If additional tweaking is necessary, then additional physical information 102 may be required to iteratively arrive at a suitable template file 106. The completed physical template has use 118, for example, modeling oil reservoir flow or in bio-engineering.

The physical information 102 is geometrical data describing physical patterns and includes boundary conditions defining a flow field within a porous media. The boundary conditions may be extracted from the field experimentally, or physically measured, e.g., computerized tomography (CT) scanning rock samples.

Suitable, well-known algorithms transform 104 the boundary conditions into a set of mathematical equations. Coding the equations using a suitable programming language, the coded equations serve as a template 106 for simultaneously simulating flow 108 and manufacturing 110 a lab-on-a-chip with representative embedded channel structures for experimental physical analysis. Lattice Boltzmann or continuous fluid dynamics methods are suitable for simulating 108 and predicting template flow behavior for represented geometric structures.

Specific channel geometries may be unrealizable within the limitations of a given manufacturing process. Critical manufacturing process parameters include, for example, construction material, channel dimensions and projected processing time. Thus, comparing design requirements for the template channel geometry with specific manufacturing requirements/limitations, preprocessing 110 determines whether the current template is manufacturable 112. If the specific channel geometry cannot be realized within the limitations of the particular manufacturing process, the template is modified accordingly, generating a new, modified template file 106. A suitable processing system layout transforms 112 a manufacturable template 106 into a standard semiconductor mask making data format, e.g., Graphic Data System (GDS) for lithographically producing template shapes 114 on a wafer, using typical state of the art semiconductor fabrication techniques, e.g. e-beam or photo-lithography and wet or dry etch.

Once fabricated, template channel flow field is measurable using suitable experimental techniques, e.g. nano-scale or micro-scale characterization tools to verify/validate the template through comparison 116 against simulation results and, if necessary, re-iterated to achieve an acceptable comparison 116. So preferably, the comparison 116 highlights simulation to physical model deviations, used in the next iteration to adjust template design until achieving the desired results, i.e., simulation to physical model deviations below an identified error threshold.

Completed preferred lab-on-a-chip assemblies include patterned two-dimensional (2D) lattice structures, electrically controlled for providing functionalities such as local heating and light emission/detection for integrated optical measurement such as chemical and biological sensing. Moreover, the 2D structures provide for controlling and monitoring liquid to solid interface surface interaction for experimentally validating and controlling surface wetting properties. Thus, the present invention integrates electrically conducting, flexible, optically transparent, ultrathin 2D materials in a fully scalable fluidic chip platform that also may be rigid or flexible. The final, preferred lab-on-a-chip results provide a basis for scaling strategies for propagating flow properties to desired lengths and scales, e.g., for oil reservoir models from the nanometer (nm) scale to the macro (six orders of magnitude larger) scale.

Figure 2A:
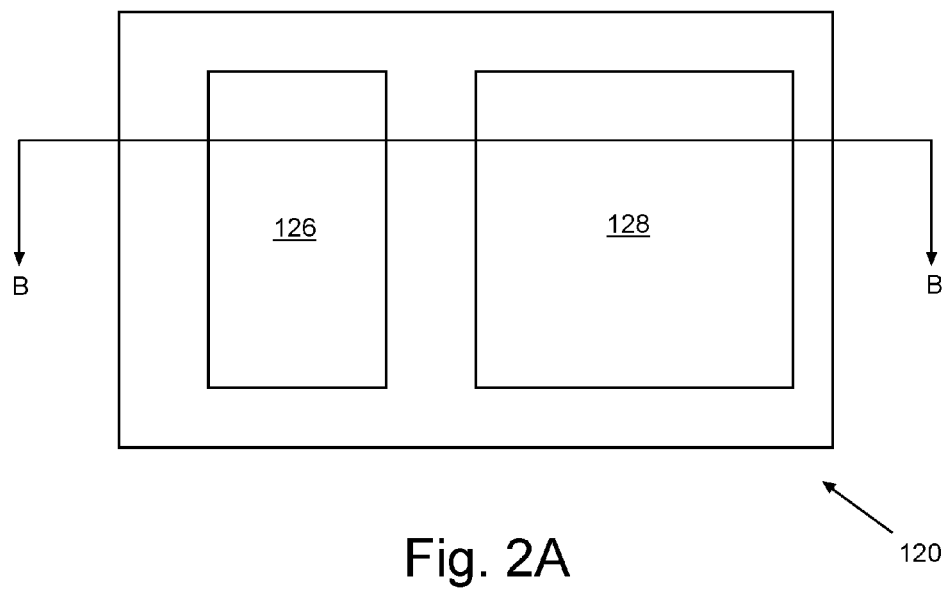
FIG. 2A shows an example of a plan view of a simple lab-on-a-chip site.
Figure 2B:
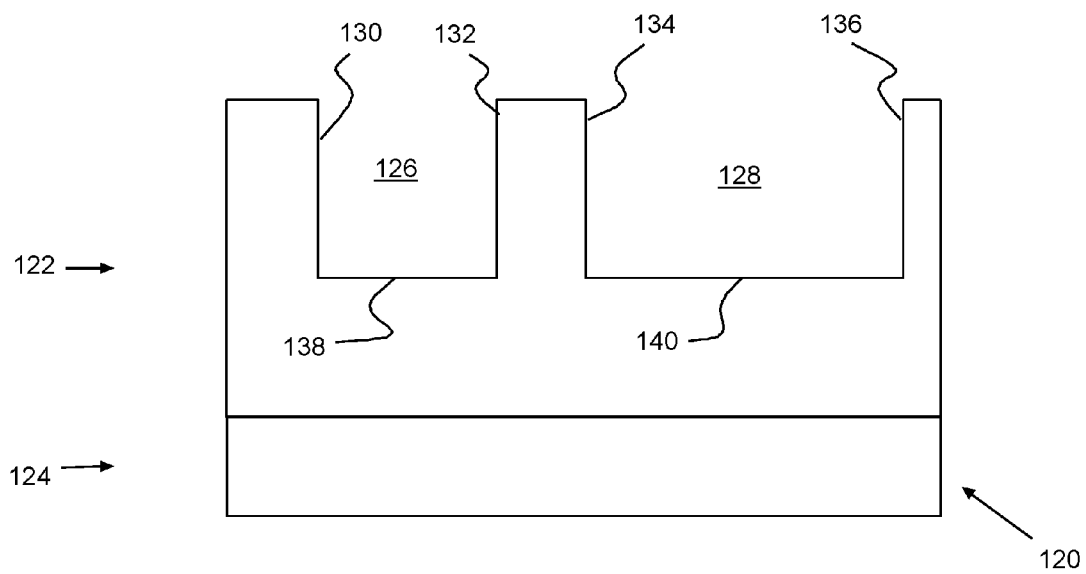
FIG. 2B shows a cross-section of the lab-on-a-chip site of FIG. 2A
Figure 3A:
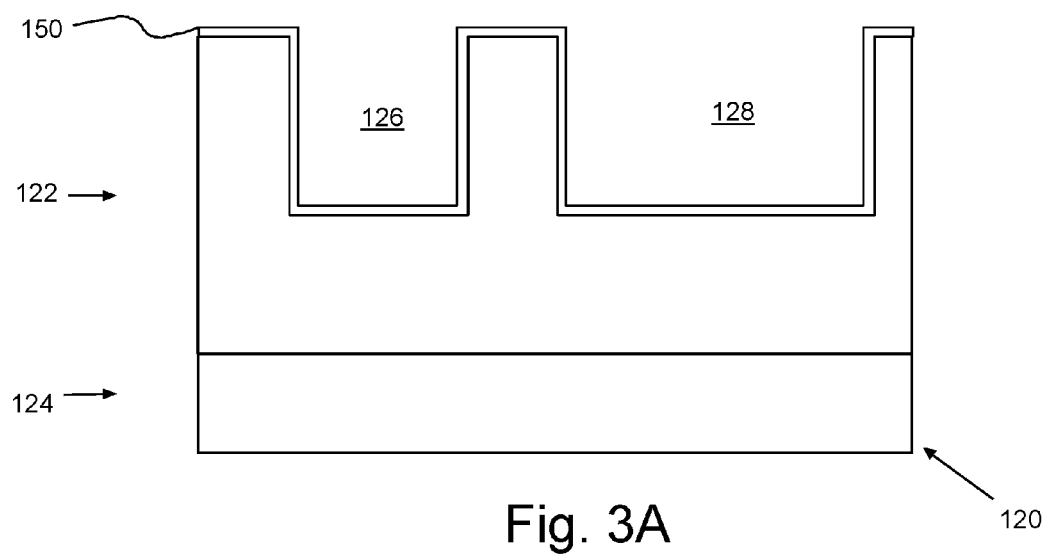
FIGS. 3A-D show an example of forming 2D support circuitry lattice structures on a lab-on-a-chip site.
Figure 3B:
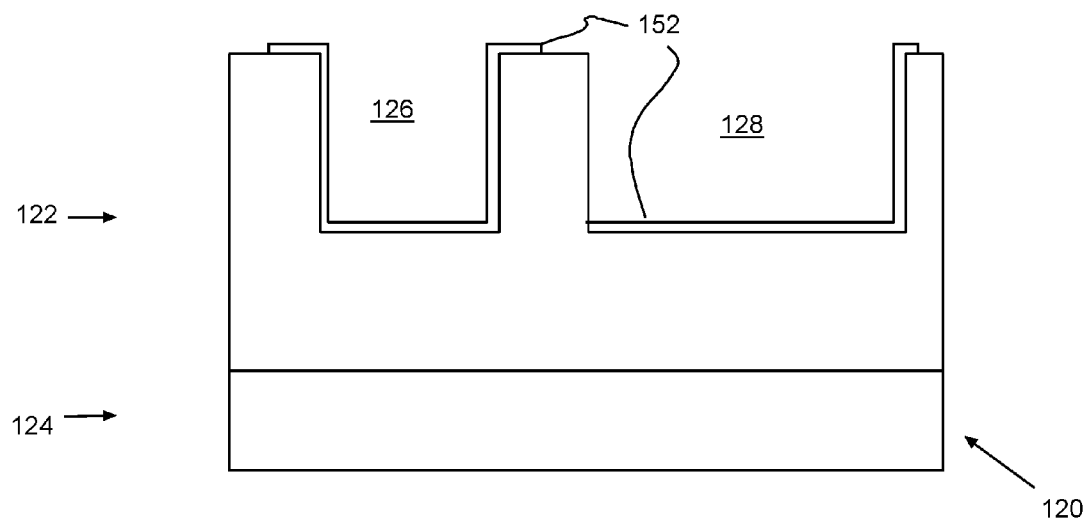
Figure 3C:
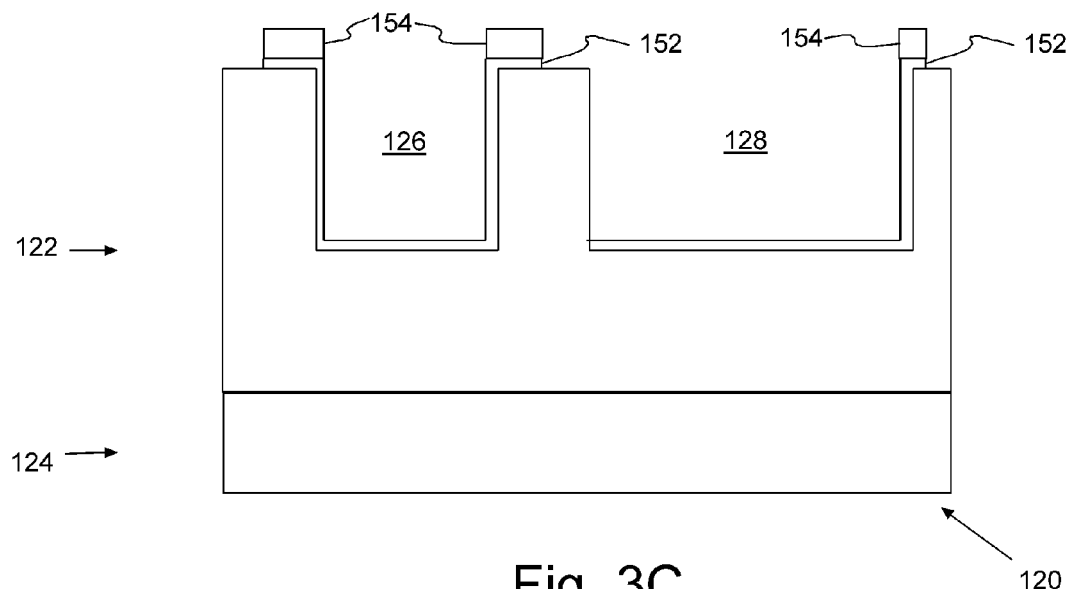
Figure 3D:
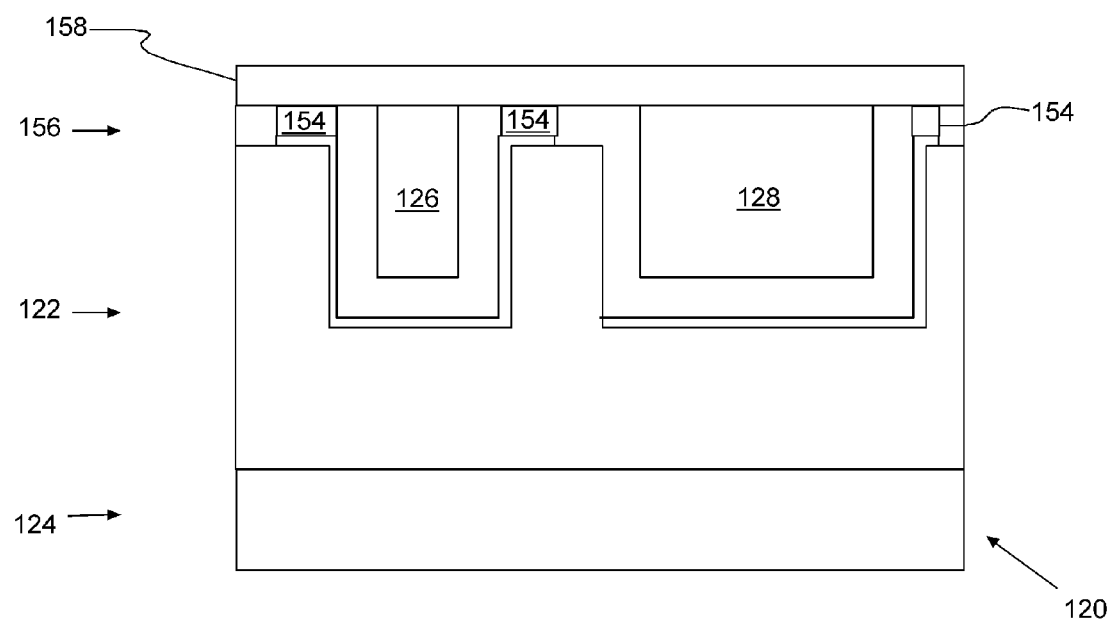

FIG. 2A shows an example of a plan view of a simple lab-on-a-chip site 120 and FIG. 2B shows a cross-section of the lab-on-a-chip site 120 of FIG. 2A through BB. In this example the site 120 is in a surface layer 122 above a substrate layer 124. Although shown here as two cavities or channels 126, 128 with different sizes, this is for example and description only. The channel shape, number and pitch is application-specific, depending on the field boundary conditions provided in 102 in FIG. 1. Thus, the channels 126, 128 may be any number of straight and/or curved cavities, uniformly sized and shaped, or irregularly sized and shaped. Preferably cavities are 1-1000 micrometers (μm or microns) long with 0.1-100 μm width and/or depth.

Further, the channels 126, 128 have planar or non-planar sidewalls 130, 132, 134, 136 and floors 138, 140, and may include obstructing features. Any included obstructing features, again on the order of 0.1-100 μm, may be, for example, pillars or blocks at the cavity sides or bottoms and may have uniform or randomized, well-defined geometric shaped cross sections, e.g., circular, triangular or rectangular cross-sections. The obstructing features may be located in the channels 126, 128, with or without periodicity and with constant or varying aspect ratios. Moreover, one or more channel 126, 128 may include partitioning walls that segment one or more of the channels 126, 128 into multiple smaller channels. For example, channel 128 may include several, regular or irregular shaped, cavity walls segmenting it into several smaller channels with the same aggregate capacity as channel 126, e.g., for comparing fluid flow through the different structures.

Although shown here as a substrate layer 124 supporting a surface layer 122, e.g., oxide grown on semiconductor, this is for example only. The substrate layer 124 may be any suitable material, or optionally, omitted. The surface layer 122 also may be any suitable material, e.g., glass, quartz, silicon carbide (SiC), silicon nitride ($Si_3N_4$), or plastics. The channels 126, 128, may be formed using lithographic techniques well known in the semiconductor manufacturing arts, e.g., soft mask or hard mask lithography. For example, the channels 126, 128 can be defined by optically or electron beam (e-beam) patterning a positive resist layer (not shown), e.g., polymethyl methacrylate (PMMA), Hydrogen silsesquioxane (HSQ), or S1818™; removing unexposed (or exposed) areas of the resist film; and etching the open areas of the surface layer 122. Thus, the mask layer may be a soft mask layer or a hard mask layer, e.g., oxide, nitride, or deposited metal. The cavity etch may be a suitable dry etch (e.g., $O_2$ and $CHF_3$) or a suitable wet etch (e.g., hydrofluoric acid) and lift-off.

Optionally, micro-particles/nano-particles or continuous or patterned thin films (not shown) deposited on cavity sidewalls 130, 132, 134, 136 and/or floors 138, 140, modify the respective surfaces. These optional surface patterns add surface interaction while maintaining the channel optical transparency for optical inspection. Thus, sidewall or floor features provide multi-phase flow patterns with wettability properties (hydrophilic/hydrophobic) based on the surface coatings used. Typical suitable such particles or thin films include dielectrics such as silicon dioxide ($SiO_2$), aluminum oxide ($Al_2O_3$), hafnium (IV) oxide ($HfO_2$), mono-layers/multi-layers of molecular compounds, and two-dimensional lattice structures, e.g., a single or a multilayer graphene, transition metal dichalcogenides, or black phosphorus.

Robust lab-on-a-chip capability includes localized heating for facilitating droplet movement and/or thermal cycling; on-chip light sources; and on-chip light detectors, and sensors. Thus preferably, the analysis support circuitry is optoelectronic and provides localized heating, light emission and detection in suitable mono-atomic, 2D lattice structures, e.g., single-layer or multi-layer organic and inorganic materials. Suitable optoelectronic circuits may include transparent 2D carbon lattice electrodes, e.g., graphene, for facilitating droplet actuation, flow sensing, and chemical/bio-sensing. Suitable circuit materials include, for example, graphene, transition metal dichalcogenides and black phosphorus. Regular arrays and random networks/thin films of quasi-one dimensional lattice structures, such as organic and anorganic nanotubes/nanowires, combine to form the 2D lattice structures.

Infrared (IR) or visible light radiation on 2-D materials can cause electrical excitation in 2-D materials. The electrical excitation in turn causes lattice vibrations that is one source of Joule heating in the 2-D materials. Thus, light radiation is useful both as an on-chip heat source for controlling/inducing Joule heating and as an radiated output, detecting visible and IR light. On-chip heating and light emission/detection may be useful for sub-micron flow field measurements. Optical applications have further use in combination with optical waveguide structures that can be integrated on or with the same lab-on-a-chip.

Molecular species in the channel flow solution interact electronically with channel walls and features, which provides a mechanism for flow sensing and chemical and bio-sensing. The molecular interaction from extreme surface-to-volume ratio of the 2-D structure modifies electrical current transport characteristics through and around the channels. Thus measuring this modification is indicative of the electrical current transport characteristics.

FIGS. 3A-D show an example of forming 2D analysis support circuitry lattice structures on the lab-on-a-chip site 120 of FIGS. 2A-B, formed by applying standard semiconductor integrated circuit (IC) manufacturing techniques. First, a layer 150 of a 2D lattice material is formed on the site 120 surface. Thus, layer 150 may be graphene or a carbon nanotube film formed on a substrate, e.g., a spin-on layer. Then, using a typical mask and etch or mask and wash, the 2D lattice layer 150 is patterned 152. Alternately, the 2D lattice layer 150 may be patterned using a lift-off or any other suitable patterning process. Next, contacts or wires 154 are formed to the 2D lattice patterns 152, again using any suitable patterning process, e.g., masking and etching a conducting layer or a standard metal lift off. Typically the wires traverse alongside the channel, partially or fully along the length, making contact to other wiring layers above or below the contact/wire 154 layer. Preferably, the contacts/wires 154 are a metal, e.g., palladium (Pd), gold (Au), titanium (Ti), tungsten (W), aluminum (Al), nickel (Ni) or an alloy thereof. An insulating layer 156 formed over the 2D lattice patterns 152 covers the template surface. Suitable insulating layer 156 materials include, for example, $SiO_2$, $Al_2O_3$, $HfO_2$, or an insulating polymer, deposited by thermal evaporation, atomic layer deposition, or spin coating. A transparent insulator cap 158 caps the cavities and completes the preferred lab-on-a-chip. The transparent insulator cap 158 may be any suitable transparent rigid or semi-rigid material, such as glass, quartz, SiC, $Si_3N_4$, or plastic, attached by a standard bonding process selected for the particular cap and template materials involved.

Locating one or more gate electrodes (not shown) below the channels 126, 128, e.g., on the surface of semiconductor substrate 124 or in surface layer 122, enables charge carrier density modulation in the 2D lattice structure for controlling localized heat generation or light emission. Also, through hole vias (not shown) may be opened through the transparent insulator cap 158 for inlet/outlet ports for filling the channels 126, 128 with fluid.

Figure 4A:
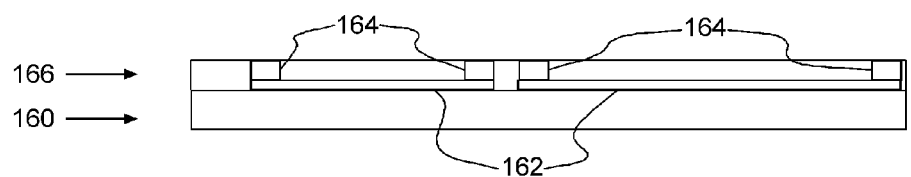
FIGS. 4A-B show an alternate example of forming 2D support circuitry lattice structures, wherein the structures are formed on the transparent insulator cap for attachment to the lab-on-a-chip site.
Figure 4B:
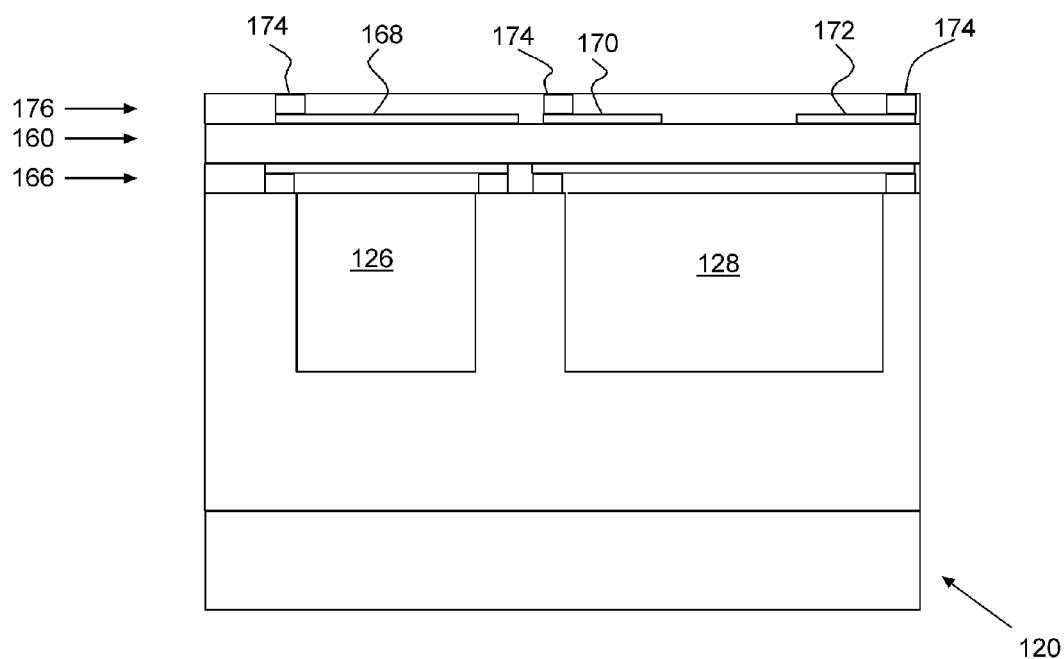

FIGS. 4A-B show an alternate example of forming 2D analysis support circuitry lattice structures, wherein the structures are formed on the transparent insulator cap 160 for attachment to the lab-on-a-chip site 120 of FIGS. 2A-B. The patterned 2D material layer 162 (graphene or a carbon nanotube film) is formed on the cap 160. Contacts 164 are formed to the 2D lattice patterns 162 and an insulating layer 166 formed over the 2D lattice patterns 162 finishes one side of the cap 160. Once complete, the insulator cap 160 is flipped, and attached. It should be noted that the structures may be formed on the template 120 as shown in FIGS. 3A-D, on the cap 160 as shown in FIGS. 4A-B or both, in combination or the same wafer or chip(s). Gates 168, 170, 172 are formed on the opposite, external surface of the insulator cap 160 in this example, and wires/contacts 174 connect to the gates 168, 170, 172. A planarized dielectric layer 176 covers the gates 168, 170, 172 between wires/contacts 174.

In this example, channel 126 with gate 168 may be configured as including a local heater or, as including a chemical or bio-sensor. Optionally, as a chemical or bio-sensor insulating layer 166 may be selectively removed between the channel 126 analyte and the 2D lattice structure. The dual or split gates 170, 172 enable charge carrier density modulation for controlling heat generation localization or for light emission/detection. Thus, channel 128 with gates 170, 172 may be configured for use as including a light emitter and/or a light detector with light passing through the bottom of the channel, coupled through an on chip integrated optical waveguide. Alternately, 2D lattice structures on opposing channel walls (not shown) may provide both a light emitter and a light detector on the same site.

Figure 5:
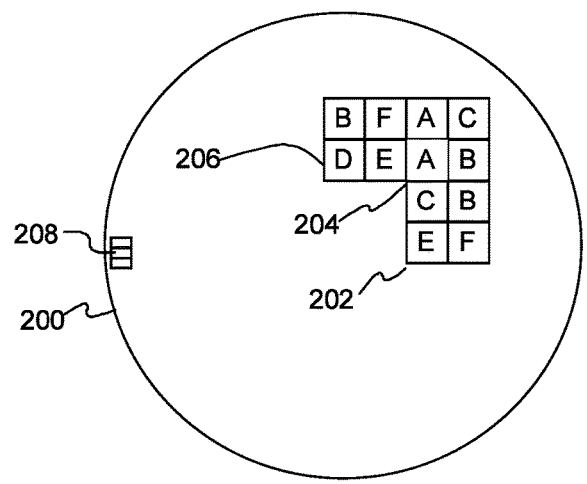
FIG. 5 shows an example of a wafer with an array of sites with templates formed in each site.

FIG. 5 shows an example of a wafer 200 with an array 202 of sites 204 with templates formed in each site 204, 206. Typically, the array 202 fills the entire wafer 202 with sites 204, 206 in each array cell location. Further, the sites may be an array of identical template locations, or an array of two or more different template locations. Thus in this example different locations are designated by a different letter, A-F. Once formed, the wafer 200 may be diced to separate all or some of the sites 204, 206 into individual labs-on-a-chip, or alternately, the entire wafer 200 may remain intact, used as a single, unified lab-on-a-chip. Further, the wafer 200 and/or the sites 204 include one or more contact pads 208 for connecting, e.g., power supply, signal and sensor probes, to site 204, 206 heaters, light sources and detectors, and sensors (not shown).

Figure 6:
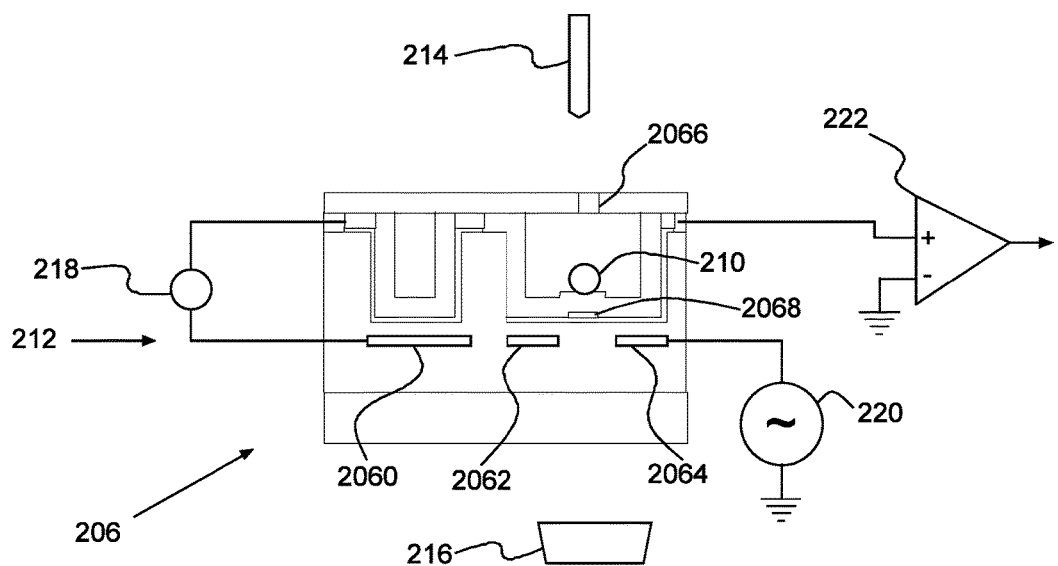
FIG. 6 shows an example of application of a lab-on-a-chip device.

FIG. 6 shows an example of application of lab-on-a-chip device 206, formed substantially similar to the lab-on-a-chip of FIGS. 2A-B and FIGS. 4A-D. In this example the lab-on-a-chip device 206 is for analyzing responses of a droplet 210 in gas or liquid. Transparent gates 2060, 2062 and 2064 are formed in gate layer 212, e.g., sub-etching the channels, depositing/growing the gates 2060, 2062 and 2064, and overfilling with the channel layer material. Transparent conductors, e.g., Indium Tin Oxide (ITO) or a two-dimensional lattice, may be sandwiched between two optically transparent insulators, e.g., glass, quartz, SiC, $Si_3N_4$ or plastics. An inlet/outlet port 2066 in the cap provides for liquid injection. Channel features 2068 in this example include a nano-particle, e.g., in a nano-particle array, on the channel floor.

A light source 214, e.g., an optical waveguide structure, is disposed above the site 206 in this example, and a light detector 216, e.g., external optical equipment such as a microscope, is disposed below the site 206. A supply 218 biases device terminals and a signal source 220 provides for inducing electronic stimulation, modulating device terminal biases or any desired for the particular application. A sensor 222, e.g., a differential amplifier, provides for sensing opto-electrical response, for example. It is understood that this device is shown for example only, and preferred labs-on-a-chip have widespread application, e.g., as bio-sensors or for hydrocarbon field studies, with exact features and structure of the actual device tailored for the needs of the particular application.

Thus, one example of an application-specific lab-on-a-chip device, surface-functionalized to serve as a local reaction chamber, may include inlet/outlet ports for liquid injection, an intra-channel pillar array, and one or more strategically located local heater(s). Other lab-on-a-chip embodiments may include features that allow for liquid sensing and surface wetting control, e.g., controlling liquid droplets (e.g., oil) interfacing with a solid under external electrical bias, while simultaneously in-situ monitoring the droplet's position and movement optically. The presence of liquid, e.g., 210, causes measurable device electrical transport property variations. Lab-on-a-chip device transparency of the ensures that an optical beam passing through the device can be steered to the position of the liquid for optical detection and analysis Thus advantageously, the present invention provides application-specific labs-on-a-chip fully integrated using state of the art scalable semiconductor manufacturing processes, while maintaining rigid or flexible fluidic chip optical transparency. Thus, the present invention has application to analyzing complex liquid system responses of the type encountered in the oil and gas, healthcare, and other liquid-handling industries, and so, reduces industrial fluid analytics research and development (R&D) costs and time-to-value. Further, the present invention provides for integration of electrically conducting, flexible, optically transparent, ultra-thin two-dimensional materials within a fully scalable fluidic chip platform. Two-dimensional lattice structures are patterned and electrically for localized heating, light emission/detection, and chemical/biological sensing for optical testing and sensing. Moreover, preferred 2D structures provide for control and for monitoring surface liquid to solid interface interactions for experimentally validating and controlling surface wetting properties, through nanometer scale wetting (nano-wetting) microscopy.

While the invention has been described in terms of preferred embodiments, those skilled in the art will recognize that the invention can be practiced with modification within the spirit and scope of the appended claims. It is intended that all such variations and modifications fall within the scope of the appended claims. Examples and drawings are, accordingly, to be regarded as illustrative rather than restrictive.

What is claimed is:

1. A method of analyzing fluid flow through a selected body, said method comprising:
    collecting data describing physical characteristics for a body;
    fabricating a lab-on-a-chip modeling said body from said data, fabricating said lab-on-a-chip comprising:
        opening one or more cavities in a channel layer,
        forming a capping layer for covering said one or more cavities, said capping layer being transparent,
        forming a two dimensional (2D) lattice structure at one surface of each of said one or more cavities, said 2D lattice structure being transparent,
        forming a gate at one said surface of at least one cavity, said gate being separated from said at least one cavity by said 2D lattice structure, and
        forming wiring connecting the gates and the 2D lattice structures externally;
    adding fluid to said cavity;
    selectively connecting biases, signals and sensors to said wiring;
    causing light to pass through said fluid;
    measuring fluid flow responses to said biases, signals and light.

2. A method as in claim 1, wherein said capping layer includes at least one input/output port above at least one cavity, said input/output port for introducing said fluid into, and removing said fluid from, said cavity.

3. A method as in claim 1, wherein biasing said gates and said 2D lattice structures causes one or more of said 2D lattice structures to generate said light being measured to pass through said fluid.

4. A method as in claim 1, wherein biasing said gates and said 2D lattice structures causes one or more of said 2D lattice structures to heats said fluid, an optical wave guide providing said light being measured to one surface of said lab-on-a-chip, said light exiting an opposite surface of said lab-on-a-chip to a detector at said opposite surface.

5. A method as in claim 1, wherein said body is a hydrocarbon reservoir, said one or more cavities including one or more structural features representative of the physical properties of said hydrocarbon reservoir, said one or more structural features obstructing fluid flow through said cavity.

6. A method as in claim 1, wherein at least one said 2D lattice structure is a local heater selectively heating said fluid at said at least one 2D lattice structure.

7. A method as in claim 1, wherein said body is a biological body.

* * * * *